"" US010543352B2

(12) United States Patent
Haag et al.

(10) Patent No.: US 10,543,352 B2
(45) Date of Patent: Jan. 28, 2020

(54) COUPLING DEVICE AND METHOD FOR USING THE SAME

(71) Applicant: MAQUET CARDIOPULMONARY AG, Rastatt (DE)

(72) Inventors: Ulrich Haag, Bisingen (DE); Ralf Engelhardt, Bodelshausen (DE)

(73) Assignee: MAQUET CARDIOPULMONARY GmbH, Rastatt (DE)

( * ) Notice: Subject to any disclaimer, the term of this patent is extended or adjusted under 35 U.S.C. 154(b) by 975 days.

(21) Appl. No.: 14/247,175

(22) Filed: Apr. 7, 2014

(65) Prior Publication Data
US 2014/0228815 A1   Aug. 14, 2014

Related U.S. Application Data

(63) Continuation-in-part of application No. PCT/EP2012/069329, filed on Oct. 1, 2012.
(Continued)

(30) Foreign Application Priority Data

Oct. 5, 2011   (DE) ........................ 10 2011 084 027

(51) Int. Cl.
*A61M 39/10* (2006.01)
(52) U.S. Cl.
CPC . *A61M 39/1011* (2013.01); *A61M 2039/1027* (2013.01); *A61M 2039/1083* (2013.01); *A61M 2039/1088* (2013.01)

(58) Field of Classification Search
CPC .......... A61M 39/00; A61M 2039/0072; A61M 39/10; A61M 39/1011; A61M 2039/1016; A61M 2039/1038; A61M 2039/1033
See application file for complete search history.

(56) References Cited

U.S. PATENT DOCUMENTS 2,597,699 A   5/1952   Bauer
3,833,013 A   9/1974   Leonard
(Continued)

FOREIGN PATENT DOCUMENTS

BE   893623 A1   10/1982
DE   2258945 A1   6/1973
(Continued)

OTHER PUBLICATIONS

International Search Report for PCT/EP2012/069329—dated Jan. 23, 2013, European Patent Office, Netherlands.
(Continued)

*Primary Examiner* — Bhisma Mehta
*Assistant Examiner* — William R Frehe
(74) *Attorney, Agent, or Firm* — Wesley Scott Ashton; Kirk D. Swenson

(57) ABSTRACT

The present invention relates to a connector system for use in connecting conduits together, such as those used with an extracorporeal blood circulation system. The system has a male and female connector and a seal. The seal is operatively associated with the male and female connectors and forms a fluid tight connection between the male and female connectors. An inner surface of the seal and the inner surfaces of the first and second coupling ends form a continuous and smooth transitional surface.

12 Claims, 9 Drawing Sheets

Related U.S. Application Data

(60) Provisional application No. 61/809,267, filed on Apr. 5, 2013.

(56) References Cited

U.S. PATENT DOCUMENTS

| | | | |
|---|---|---|---|
| 3,834,124 A | 9/1974 | Ichikawa | |
| 4,004,587 A | 1/1977 | Jess | |
| 4,143,423 A | 3/1979 | Sternlieb | |
| 4,177,808 A | 12/1979 | Malbec | |
| 4,361,380 A | 11/1982 | Marazzi | |
| 4,493,705 A | 1/1985 | Gordon et al. | |
| 4,526,572 A | 7/1985 | Donnan et al. | |
| 4,568,333 A | 2/1986 | Sawyer et al. | |
| 4,615,694 A | 10/1986 | Raines | |
| 4,636,196 A | 1/1987 | Tsuji et al. | |
| 4,643,713 A | 2/1987 | Viitala | |
| 4,668,217 A | 5/1987 | Isono | |
| 4,738,668 A | 4/1988 | Bellotti | |
| 4,820,288 A | 4/1989 | Isono | |
| 4,863,452 A | 9/1989 | Irmiter et al. | |
| 4,888,004 A | 12/1989 | Williamson et al. | |
| 4,935,010 A | 6/1990 | Cox et al. | |
| 5,052,725 A | 10/1991 | Meyer et al. | |
| 5,135,264 A | 8/1992 | Moore | |
| 5,147,298 A | 9/1992 | Turner et al. | |
| 5,290,246 A * | 3/1994 | Yamamoto | A61M 25/0014 604/167.03 |
| 5,312,352 A | 5/1994 | Leschinsky et al. | |
| 5,439,448 A | 8/1995 | Leschinsky et al. | |
| 5,456,676 A | 10/1995 | Nelson et al. | |
| 5,507,731 A | 4/1996 | Hernandez et al. | |
| 5,607,406 A | 3/1997 | Hernandez et al. | |
| 5,628,726 A | 5/1997 | Cotter | |
| 5,674,200 A | 10/1997 | Ruschke et al. | |
| 5,680,859 A | 10/1997 | Urion et al. | |
| 5,693,025 A | 12/1997 | Stevens | |
| 5,799,987 A | 9/1998 | Sampson | |
| 5,845,943 A | 12/1998 | Ramacier et al. | |
| 5,851,201 A | 12/1998 | Ritger et al. | |
| 5,938,244 A | 8/1999 | Meyer | |
| 6,024,124 A | 2/2000 | Braun et al. | |
| 6,066,111 A | 5/2000 | Brockhoff | |
| 6,082,401 A | 7/2000 | Braun et al. | |
| 6,217,556 B1 * | 4/2001 | Ellingson | A61B 10/0283 604/167.01 |
| 6,217,560 B1 | 4/2001 | Ritger et al. | |
| 6,312,414 B1 | 11/2001 | Brockhoff et al. | |
| 6,447,481 B1 | 9/2002 | Duchon et al. | |
| 6,613,012 B2 | 9/2003 | Kraushaar | |
| 6,827,862 B1 | 12/2004 | Brockhoff et al. | |
| 7,040,586 B2 | 5/2006 | Kusber et al. | |
| 7,052,047 B1 * | 5/2006 | Box | F16L 59/184 285/123.15 |
| 7,080,665 B2 | 7/2006 | Whall | |
| 7,097,690 B2 | 8/2006 | Usher et al. | |
| RE39,668 E | 5/2007 | Bagaoisan et al. | |
| 7,338,476 B2 | 3/2008 | Kraushaar | |
| 7,434,842 B2 | 10/2008 | Schmidt | |
| 7,438,699 B2 | 10/2008 | Pecor et al. | |
| 7,455,662 B2 | 11/2008 | Kraushaar | |
| 7,828,336 B2 | 11/2010 | Gammons | |
| 7,854,828 B2 | 12/2010 | Reid et al. | |
| 7,892,209 B2 * | 2/2011 | Harand | A61M 16/0463 604/167.01 |
| 8,092,416 B2 | 1/2012 | Duenas | |
| 8,157,758 B2 | 4/2012 | Pecor et al. | |
| 8,308,931 B2 | 11/2012 | Reid et al. | |
| 8,475,636 B2 | 7/2013 | Mayer et al. | |
| 8,475,644 B2 | 7/2013 | Mayer et al. | |
| 2004/0223872 A1 * | 11/2004 | Brian | A61M 1/1698 422/45 |
| 2004/0230169 A1 * | 11/2004 | Felix | A61M 1/0047 604/317 |
| 2004/0241041 A1 * | 12/2004 | Woodworth | A61J 1/1406 422/22 |
| 2005/0082828 A1 | 4/2005 | Wicks et al. | |
| 2007/0249197 A1 * | 10/2007 | Spranger | A61M 39/1011 439/152 |
| 2009/0127288 A1 | 5/2009 | Keller | |
| 2009/0188575 A1 * | 7/2009 | Williams | F16L 37/0985 137/798 |
| 2010/0025989 A1 | 2/2010 | McKeon, III | |

FOREIGN PATENT DOCUMENTS

| | | |
|---|---|---|
| DE | 3300203 A1 | 7/1984 |
| DE | 102011084027 A1 | 4/2013 |
| EP | 305364 B1 | 2/1993 |
| EP | 954364 A1 | 11/1999 |
| WO | 1999020322 A1 | 4/1999 |
| WO | 2008058134 A2 | 5/2008 |
| WO | 2013050319 A1 | 4/2013 |
| WO | 2013092418 A2 | 6/2013 |

OTHER PUBLICATIONS

English Translation of the Written Opinion of the International Search Authority—dated Apr. 5, 2014, European Patent Office, Netherlands.

Written Opinion of the International Search Authority for PCT/EP2012/069329—dated Apr. 5, 2014, European Patent Office, Netherlands.

English Translation of International Search Report for PCT/EP2012/069329—dated Jan. 23, 2013, European Patent Office, Netherlands.

Office Action for DE102011084027A1, German Patent Office—dated Jun. 22, 2012, Germany.

The American Heritage Desk Dictionary 175 (1981).

International Preliminary Report on Patentability issued in International Application No. PCT/EP2012/069329, dated Apr. 8, 2014.

Communication issued in European Application No. 12766659.2, dated Jun. 26, 2014.

Examination Report issued in European Application No. 12766659.2, dated Jan. 11, 2016.

* cited by examiner

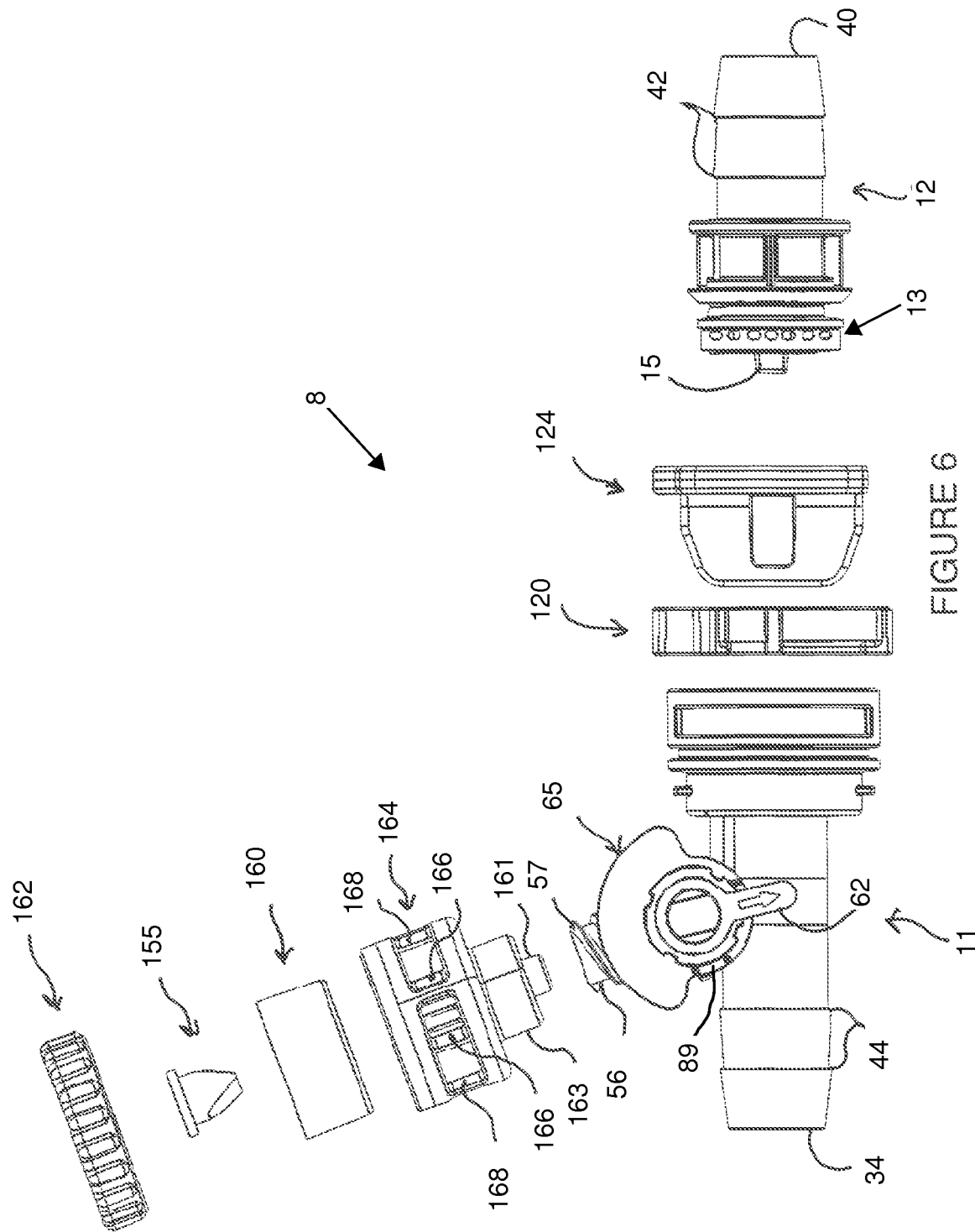

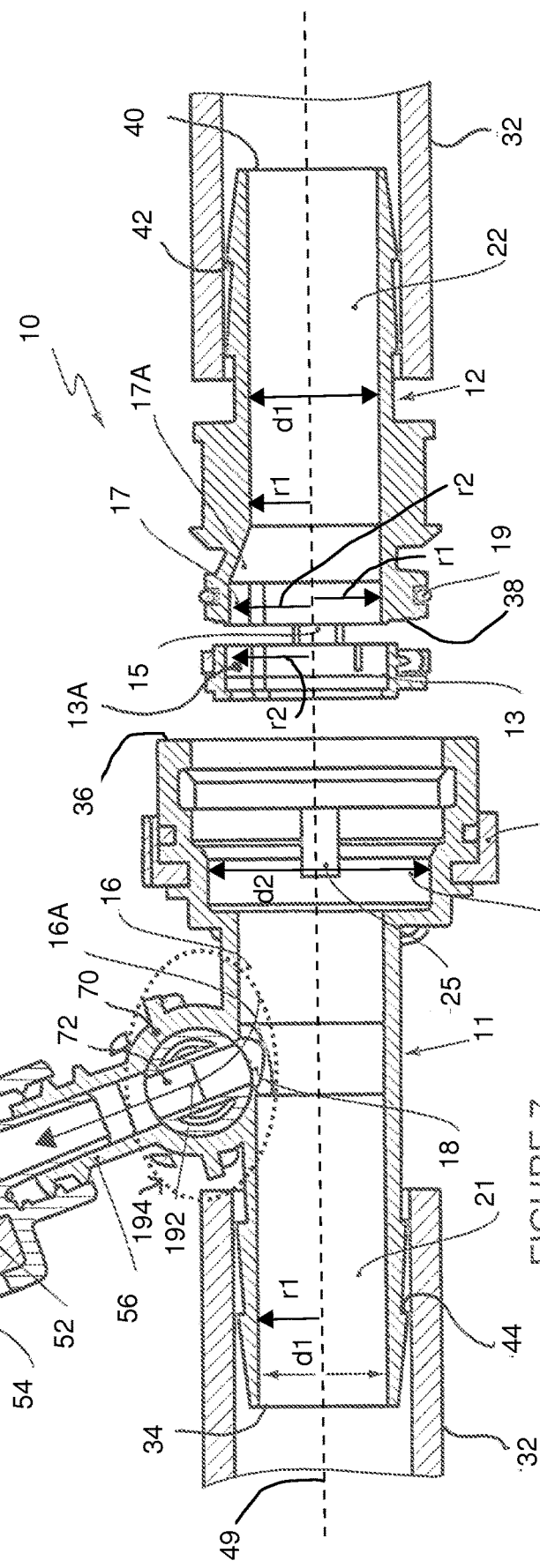
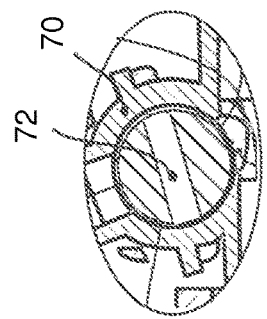
FIGURE 10
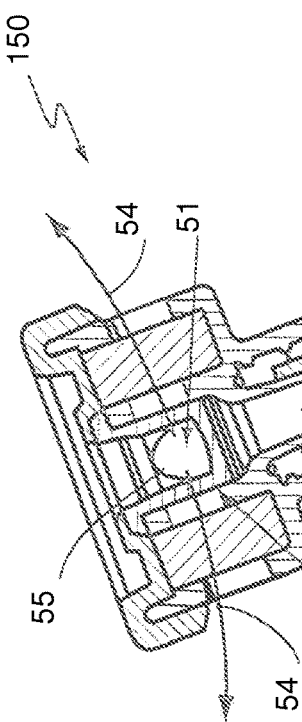
FIGURE 7

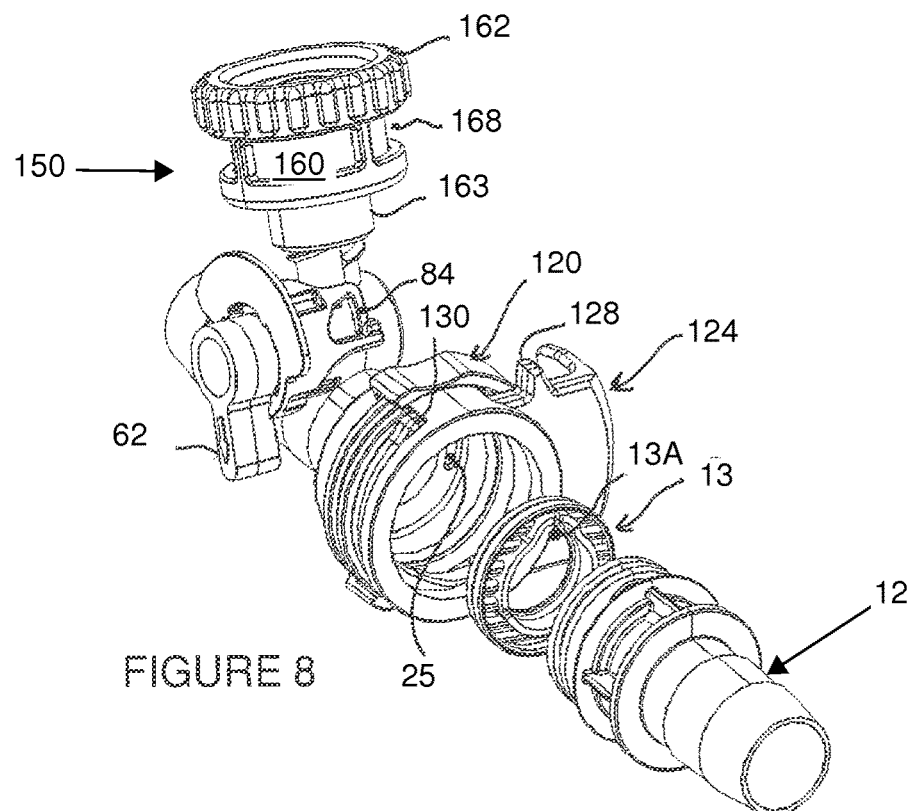
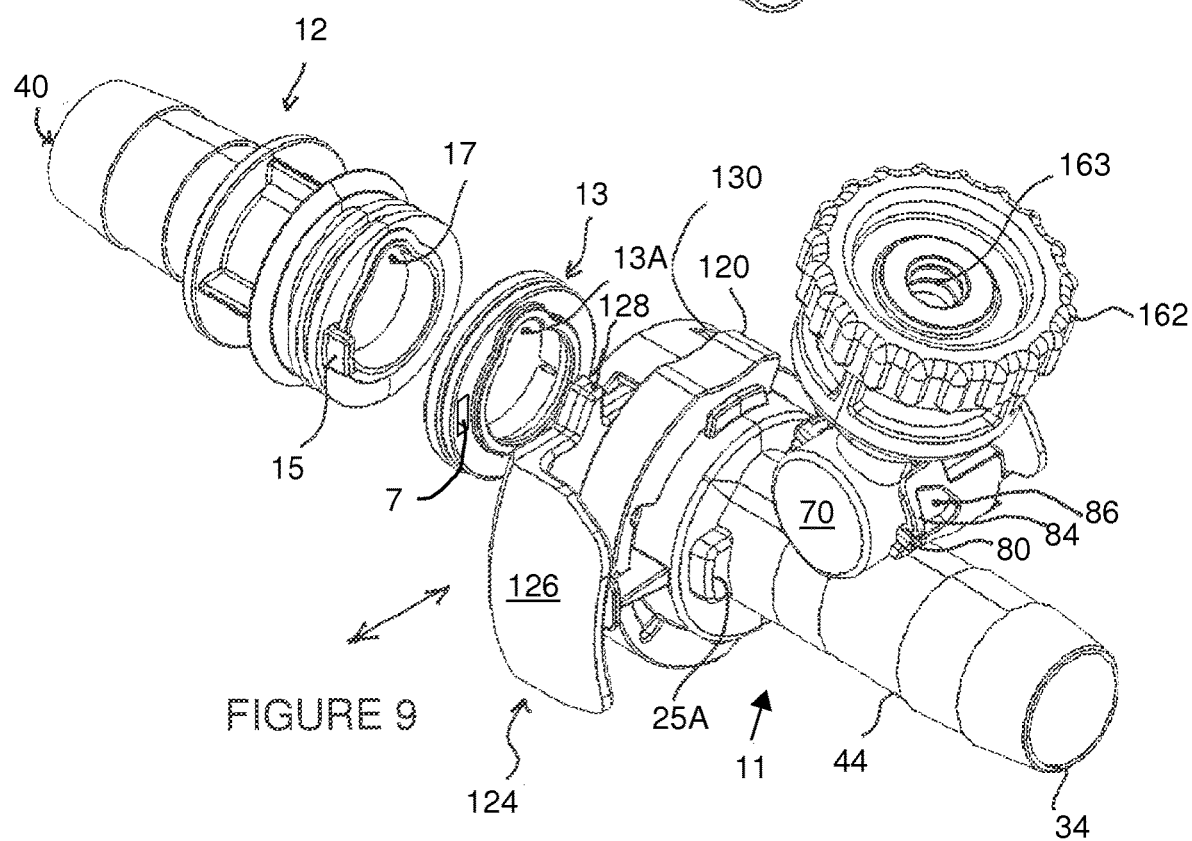

COUPLING DEVICE AND METHOD FOR USING THE SAME

CROSS-REFERENCE TO RELATED APPLICATIONS

The present application is a continuation-in-part application filed under 35 USC § 111(a), and (i) claims the benefit of priority under 35 USC § 365(c) and § 120 to PCT Application number PCT/EP2012/069329, filed Oct. 1, 2012, which claims the benefit of priority to German patent application serial number DE201110084027, filed on Oct. 5, 2011, now published as DE102011084027A1, and (ii) claims priority under 35 USC § 119 to U.S. Provisional Patent Application Ser. No. 61/809,267 filed on Apr. 5, 2013, all of which are incorporated by reference herein in their entireties.

BACKGROUND OF THE INVENTION

Field of the Invention

Embodiments of the present invention relate to devices, assemblies and methods useful for creating a fluid-tight connection among fluid conduits, especially those relating to extracorporeal blood circuits. More specifically, the present invention relates to a self-sealing and/or valved coupling device, preferably of the quick-release type, for connecting flexible fluid conduits (e.g., hoses or pipe lines), preferably those adapted to carry blood to be useful for extracorporeal blood circulation systems.

Description of Related Art

In fluid circuits with hoses, catheters, cannulas, pipes or other types of fluidic conduits are utilized, individual components or portions of a fluid circuit can be connected, disconnected, and replaced one or more times depending on the specific application or procedure. Particularly in extracorporeal blood circuits, such an exchange of components is commonly performed one or more times in a single medical procedure. If not performed properly or carefully, the exchange of components may place the patient at risk for one or more complications.

Conventional connectors and couplings require a relatively large amount of operator time to carefully separate and connect new components to a blood circuit. Occasionally an actual separation of a connected hose may accidentally occur and require user intervention to reconnect the coupling. Some procedures require a brief interruption of blood flow through connected conduits in order to change or reconnect the conduits in a properly performed manner. This is done to minimize the exposure of the inner surfaces of the blood circuit to sources of external contamination to thereby prevent or reduce the patient's exposure to foreign contaminants and pathogens such as viruses or bacteria which may lead to a blood infection.

Conventional non-medical couplings such as the quick-release coupling embodiment shown in U.S. Pat. No. 5,052,725 to Meyer et al. are not suitable for certain medical applications. The patent describes a hose coupling which is detachable and can be locked and unlocked during use. One shortcoming of the coupling of the Meyer et al. embodiment relates to an interrupted and discontinuous transition region of the luminal wall between the male and female coupling members. The clearance between the male and female coupling members is relatively large, so that a gap is formed which may trigger or contribute to a plurality of clinical issues.

For instance, when the gap is filled with blood as typical during a cardiopulmonary bypass operation, the high flow rates of blood when crossing the gap may expose the blood to excessive shear stresses and turbulent flow conditions resulting in subsequent hemolysis or alternatively enhanced platelet activation. Another potential issue relating to a gap may be that of localized stagnation of blood. When local regions of blood stagnation form even as the bulk flow of blood through a region is dynamic and constantly moving, that portion of blood that is collected or stuck in the gap can lead to localized formation of blood clots as well as enhanced platelet activation and clotting.

In addition to the aforementioned clinical shortcomings, the Meyer et al. embodiment may also suffer from additional procedural complexity and ease-of-use shortcomings. In order to eliminate or minimize the introduction of air or air bubbles into a fluidic system while assembling the coupling, the male and female coupling portions of the Meyer et al. embodiment will commonly be connected while submersed in a liquid. This is done to displace air that would otherwise be introduced into the system if not performed while submerged. Even when such care is taken to connect a female and male coupling, small amounts of air bubbles may still form or gather within localized pockets or dead-spaces created by the coupling's joints. In blood circuits or systems where air bubbles remain in the system's fluid paths and are not properly removed, severe harm can be done to the patient.

SUMMARY OF THE INVENTION

To solve the above-described problems, embodiments of the present invention and disclosure provide a quick-release and/or self-sealing coupling device and assembly useful for flexible fluid carrying conduits, hoses or pipe lines, in particular for the types used in extracorporeal blood circulation systems and circuits.

The coupling device comprises a male and a female coupling piece or element which can be detachably connected to one another in a fluid tight manner, characterized in that a compliant and form-fitting seal is insertable, preferably without play and movement in a radial and an axial direction, into a correspondingly shaped opening in the female coupling piece when disposed at the connecting or mating end of the male coupling member, resulting in a gap-free and step-free transition between the fluid-conducting cavities or lumens of the two coupling members once the coupling members have been connected.

With the quick-release coupling device according to the invention, a rapid exchangeable system for the replacement of components in the fluid circuit is possible without compromising blood quality due to shear forces induced by turbulent blood flow. The laminar flow of the fluid (blood) is thus maintained. In the coupling region where the lumens of the male and female coupling elements are brought into proximity and alignment, the contour and gentle transitions of the lumen surfaces are configured to avoid gaps or steps that would potentially lead to blood damage or patient harm.

In embodiments of the present invention, a seal member is located on the male coupling member and is advantageously made of a flexible, compliant and resilient material such as silicone rubber, natural rubber, nitrile butadiene rubber (NBR), carboxylated nitrile butadiene rubber (XNBR) or recognized equivalent elastomers. The material of the seal member is particularly chosen to allow for the seal member to fill in and be able to conform to the correspondingly shaped cavity of the female coupling member and drastically reduce or eliminate axial and radial movement as well as and radially outward "backlash" or "slop" between the male and female coupling members.

To prevent the escape of any fluid, it is also advantageous to place between the male and female coupling members an additional O-ring seal. The O-ring seal is preferably located on the external surface of the male connector member and establishes a secondary seal with the corresponding internal surface of the female connector member. In particular, the quick-coupling device when used in extracorporeal blood circuits of the present invention provides further significant advantages when the coupling pieces have an interior portion or channel with an enlarged relative spacing or diameter as compared to the hose inner luminal diameter regions, as well as reversibly closable vent hole provided within this enlarged interior region. In the area of enlarged inside diameter or space/channel, an accumulation of gas bubbles can form, which can be directly aspirated through the vent opening to the outside. In the bloodstream, even the smallest gas bubbles must be avoided, as otherwise embolisms may occur. Since not all of the components in an extracorporeal blood circuit have their own ventilation means or possibilities, the use of a vent in the region of a quick-connect coupling is very desirable. In an example embodiment, the vent opening can be locked, providing assurance that a particular valve setting (i.e., open or closed) has been chosen. The user can be assured that after ventilation of trapped gas or air bubbles has occurred, no fluid will further escape through the vent opening.

In an additional example embodiment, the region of enlarged inner diameter cannot be rotated as it may not have a symmetrical profile with respect to the longitudinal axis of the corresponding male or female coupling members. Preferably, the enlarged inner diameter region may be formed by an upper region of the coupling pieces arranged along a longitudinal channel. In such an embodiment, the gas bubbles may accumulate at low flow rates in the region of expanded diameter and are capable of being directed entirely through the vent opening when the coupling device is properly oriented. In particular, this non-rotationally symmetrical design of the expanded diameter region is advantageous when the two coupling pieces can be connected together to prevent rotation, thereby allowing for the gas-collecting area of the two coupling members to be held securely in the required aligned position.

The vent opening can be in the region of one of the channel ends, and is preferably located on the female connector member, but in other embodiments may be located on the male connector member. The accumulated gases are then passed through the existing channel to the vent opening and can be removed in a fast and effective manner.

To avoid the induction of turbulence or cavitation in the fluid flow, it is also advantageous if the channel at each of its ends has a gradual transition to the internal lumens of the male and female connecting members.

Embodiments of the present invention also relate to a ventilation device for use in hose, catheter or pipe lines, in particular for connection to a quick-connect coupling device according to any one of embodiments described herein. The quick-connect coupling preferably may be releasably connected with a vent opening of the line or of the quick coupling device and have a cavity in which a porous material (e.g., a porous plug) or a semi-permeable membrane is disposed. This venting device permits an automatic venting of the lines or other fluid processing components. If the venting device is provided on a self-sealing/quick-release coupling device, then venting is carried out automatically once the coupling is closed and provided that the inside of the coupling is in fluid communication with the venting device and not blocked by a valve. The ventilation device may also utilize a luer-lock connection associated with each ventilation opening of a fluid line or a fluid handling component. The ventilation device according to the invention can also be operated manually, either in addition to the aforementioned automatic venting or as an alternative. The porous material or the porous membrane can be made of a hydrophobic material, in particular polyethylene, polypropylene or Teflon. Such a material or membrane can allow for the passing of gases and certain liquids, but restricts passage of certain hydrophilic liquids such as blood, which are blocked due to their surface tension. Compact porous materials can be produced from the previously mentioned substances, for example by powder sintering of said substances. When membranes are used, they can be reinforced as needed by means of a support element. When a mixture of a hydrophilic liquid and gas strikes such a porous surface, the gas is able to escape or pass through it, whereas the liquid is unable to wet the pores and therefore cannot penetrate through or to the outside of the porous surface. When used in blood circulation systems, blood is therefore prevented from escaping and being exposed to external surfaces or environments during the venting process, which could otherwise lead to contamination and infection of the blood and the patient when the blood is returned to the patient.

In one advantageous embodiment, the venting device can have an access aperture or port for introducing a fluid from the outside into the flexible hose line or tubing. The access port can also be used for the removal of fluid as in drawing blood samples for diagnostic purposes. Such an access allows drugs to be introduced into the blood circulation system. Blood samples can also be drawn without requiring additional cannulation of the patient. The access can be formed by a valve and is preferably configured as a female luer port arranged at an end of the cavity. Preferably, the valve is embodied or configured to open when a device with a male luer such as the syringe tip of a syringe barrel is introduced into the port, and automatically seals once the male luer is removed. Examples of such a valve may include a slit valve or duct-bill valve as offered by Vernay of College Park, Ga. When a syringe is inserted to contact the valve, the slit in the valve opens, thereby allowing the user to administer drugs or draw samples with the syringe. Once the syringe has been removed, the valve closes again automatically (i.e., self-seals). Alternate types of valves may be employed as well, including for instance displacement type luer activated valves. Examples of such valves are shown, for example in US patent publication US2002/0002351, application Ser. No. 09/810,087 filed Mar. 16, 2001, herein incorporated by reference in its entirely.

A connector system for use in connecting conduits of an extracorporeal blood circulation system according to an example embodiment of the present invention, wherein the system has a male connector comprising a first coupling end comprising an inner surface defining an opening in communication with a lumen of the male connector; and a second end for establishing fluid communication with a first conduit securable with respect to the male connector. The connector system has a female connector comprising a second coupling end comprising an inner surface defining an opening in communication with a lumen of the female connector and detachably connectable to the first coupling end. The connector system also has a second end for establishing fluid communication with a second conduit and a seal operatively associated with the male and female connectors, wherein the seal is connected to at least one of the male and female connectors such that when the male and female connectors are coupled with respect to each other, the seal is disposed between a portion of the first and second coupling ends, forming a fluid tight connection between the male and female couplers. An inner surface of the seal and the inner surfaces of the first and second coupling ends form a continuous and smooth transitional surface.

According to an example embodiment, the seal is connected to the male connector when the male and female connectors are not coupled to each other.

According to an example embodiment, the seal is fixedly positioned with respect to a portion of the first and second coupling ends to inhibit or prevent movement in a radial and axial direction when the seal is secured between the male and female couplers.

According to an example embodiment, the male and female connectors has a key and the other of the male and female connectors has a key slot for receiving the key such that the key is engaged with the key slot when the male and female connectors are coupled.

According to an example embodiment, the seal is adapted to not block the key from engaging the key slot.

According to an example embodiment, the engagement between the key and the key slot when the male and female connectors are coupled restricts radial movement of the male and female connectors with respect to each other.

According to an example embodiment, the seal comprises a flexible, resilient material.

According to an example embodiment, the continuous and smooth transitional surface is flush.

According to an example embodiment, a second seal configured as an O-ring type-seal is located on one of the male and female connectors such that the second seal establishes intimate contact with the male and female connectors at a different location than the seal.

According to an example embodiment, the openings of the first coupling end and the second coupling end are not radially symmetric.

According to an example embodiment, the inner surface of the seal is not radially symmetric.

According to an example embodiment, a vent aperture permits venting of fluid from the lumens of the male and female connectors when the male and female connectors are coupled together.

According to an example embodiment, the male and female connectors when assembled have an upright orientation and further comprising a cavity extending between one or both of the male and female connectors such that the cavity is at an elevation superior to the lumens of the male and female connectors when the connector is in the upright orientation.

According to an example embodiment, other than the inner surface of the seal and the inner surfaces of the first and second coupling ends, but not the cavity, have a cross-sectional profile when viewed in a direction normal to an axis of the connector system that substantially continuously curved.

According to an example embodiment, the cross-sectional profile is substantially circular.

According to an example embodiment, the cross-sectional profile is substantially elliptical.

According to an example embodiment, the connector system additionally has a vent aperture in one or both of the male and female connectors, wherein the vent aperture's location is at an elevation equal to or superior to the cavity.

According to an example embodiment, the connector assembly as a valve in fluid communication with the vent aperture.

According to an example embodiment, the connector assembly has at self-sealing porous material that permits gas to pass therethrough.

According to an example embodiment, the porous material is hydrophobic.

According to an example embodiment, the porous material is configured to not readily permit the movement of blood therethrough.

According to an example embodiment, the self-sealing porous material is disposed within a vent assembly connectable to the connector system.

According to an example embodiment, the connector system, the cavity is configured as a channel having a length longer than its width.

According to an example embodiment, the channel has ends that are gradually contoured to the lumens of the male and female connectors.

According to an example embodiment, the connectors are sterilized to a sterility assurance level or equal to or greater than 10-3 SAL, and wherein the fluidic conduits are part of an extracorporeal blood circulation system.

According to an example embodiment, the extracorporeal blood circulation system comprises a motorized pump and at least one of an oxygenator, a heat exchanger for controlling the temperature of blood passing through the extracorporeal blood circulation system, a cardiotomy reservoir, and a bubble sensor.

According to an example embodiment, the valve opens and closes via rotational movement of a knob.

According to an example embodiment, the connector system has a valve lock configured to allow at least partial rotation of the knob to open and close the valve when the lock is moved from a first position to a second position.

According to an example embodiment, the lock is biased to the first position when the valve is located in one or both of the open and closed positions.

According to an example embodiment the valve is a self-sealing valve.

According to an example embodiment, the self-sealing valve is a duck-bill valve, a luer-activated valve, or a slit valve.

According to an example embodiment, a self-sealing porous material at least partially surrounds the self-sealing valve.

According to an example embodiment, the valve is a stop-cock valve moveable from an opened position to a closed position, and a second valve, the second valve in fluid communication with the vent aperture when the stop-cock valve is arranged to the opened position.

A connector system for use in connecting conduits of an extracorporeal blood circulation system according to an example embodiment of the present invention has a male connector having a first coupling end comprising an inner surface defining an opening in communication with a lumen of the male connector; and a second end for establishing fluid communication with a first conduit securable with respect to the male connector. The connector system has a female connector comprising a second coupling end comprising an inner surface defining an opening in communication with a lumen of the female connector and detachably connectable to the first coupling end; and a second end for establishing fluid communication with a second conduit; and a cavity for collecting air bubbles in a concentrated space when blood carrying air bubbles passes through the lumens, the cavity having an elevation higher than all other portions of the lumens when the connector is in an upright orientation.

According to an example embodiment, the cavity extends at least partially lengthwise between the male and female connectors.

According to an example embodiment, the cavity traverses a luminal interface of the male and female connectors.

According to an example embodiment, the connector assembly has a vent through a sidewall of at least one of the male and female connectors, the vent allowing for air bubbles within the cavity to migrate to an elevation higher than the cavity.

A method according to an example embodiment of the present invention for connecting to fluid conduits with a connector assembly, the connector assembly having a male and female connector member configured to mate to each other and establish a fluid-tight seal therebetween, each of the male and female connector members having a lumen, the lumens substantially aligned with respect to each other when the male and fame connectors are mated, the connector assembly further comprising a cavity extension extending more radially outward than remaining portions of the lumens, the method involving the steps of maintaining for a period of time the connector assembly in an orientation such that the cavity has an elevation superior to the remaining portions of the lumens; and venting air bubbles captured within the cavity to a location exterior to the lumens.

According to an example embodiment, the method includes a step of flowing blood through the connector assembly.

According to an example embodiment, the method includes a step of exposing the blood to a porous material configured to allow for gas to pass through the plug but not allow for blood to pass through the material.

According to an example embodiment, the method includes a step of reducing the entrapment of air within the connector assembly without fully or partially disassembling the male and female connector members while submerged in a liquid.

According to an example embodiment, the method includes a step of reducing the entrapment of air within the connector assembly without assembling the male and female connector members while submerged in a liquid.

According to an example embodiment, the method includes a step of opening and closing a valve interposed between a vent aperture and the porous material.

A connector system for use in connecting conduits of an extracorporeal blood circulation system according to an example embodiment of the present invention has a male connector, a female connector, and a seal. The male connector has a first coupling end comprising an inner surface defining an opening in communication with a lumen of the male connector; and a second end for establishing fluid communication with a first conduit securable with respect to the male connector. The female connector has a second coupling end comprising an inner surface defining an opening in communication with a lumen of the female connector and detachably connectable to the first coupling end; and a second end for establishing fluid communication with a second conduit. The seal is operatively associated with the male and female connectors, and is connected to at least one of the male and female connectors such that when the male and female connectors are coupled with respect to each other, the seal is disposed between a portion of the first and second coupling ends, forming a fluid tight connection between the male and female couplers. An inner surface of the seal and the inner surfaces of the first and second coupling ends form a continuous and smooth transitional surface. The connector assembly has an upright orientation and further comprises a cavity extending between the male and female connectors such that the cavity is at an elevation superior to the lumens of the male and female connectors when the connector is in the upright orientation. The cavity is configured as a channel having a length longer than its width. The channel has at one or both of its ends a surface gradually contoured to the lumens of the male and female connectors.

A connector system for use in connecting conduits of an extracorporeal blood circulation system according to an example embodiment of the present invention has a male connector, a female connector, and a seal. The male connector has a first coupling end comprising an inner surface defining an opening in communication with a lumen of the male connector; and a second end for establishing fluid communication with a first conduit securable with respect to the male connector. The female connector has a second coupling end comprising an inner surface defining an opening in communication with a lumen of the female connector and detachably connectable to the first coupling end; and a second end for establishing fluid communication with a second conduit. The seal is operatively associated with the male and female connectors. The seal is positionable between the male and female connectors such that when the male and female connectors are coupled with respect to each other, the seal is disposed between a portion of the first and second coupling ends, forming a fluid tight connection between the male and female couplers. When the connector assembly is oriented in an upright orientation, a cavity extending between the male and female connectors and in fluid communication with the lumens is at an elevation superior to the lumens of the male and female connectors. The cavity is configured as a channel that tapers at one or both of its ends towards and is continuous with the lumens of the male and female connectors.

BRIEF DESCRIPTION OF THE DRAWINGS

FIG. 6 is a side elevation view of the embodiment of FIG. 5.

FIG. 7 is a side elevation cross-section of the coupling assembly in accordance with an exemplary embodiment of the present invention.

FIG. 8 is an isometric front view of a quick-release coupling in accordance with an exemplary embodiment of the present invention.

FIG. 9 is an isometric rear view of the embodiment of FIG. 8.

FIG. 10 is a partial view of the embodiment of FIG. 7 taken about border 194 and showing a different orientation of the thru-hole bore of the valve of FIG. 7 with respect to the socket of the female connector member.

DETAILED DESCRIPTION OF THE PRESENT INVENTION

For illustrative purposes, the principles of the present invention are described by referencing various exemplary embodiments. Although certain embodiments of the invention are specifically described herein, one of ordinary skill in the art will readily recognize that the same principles are equally applicable to, and can be employed in other systems and methods. Before explaining the disclosed embodiments of the present invention in detail, it is to be understood that the invention is not limited in its application to the details of any particular embodiment shown. Additionally, the terminology used herein is for the purpose of description and not of limitation.

Furthermore, although certain methods are described with reference to steps that are presented herein in a certain order, in many instances, these steps may be performed in any order as may be appreciated by one skilled in the art; the novel method is therefore not limited to the particular arrangement of steps disclosed herein.

For purposes of the description hereinafter, the words "upper," "lower," "right," "left," "vertical," "horizontal," "top," "bottom," "lateral," "longitudinal," "axial," and like terms, if used, shall relate to the embodiments of the present disclosure, as they are is oriented in the Figures.

It should be noted that as used herein and in the appended claims, the singular forms "a", "an", and "the" include plural references unless the context clearly dictates otherwise. Thus, for example, reference to "a coupling member" may include a plurality of coupling members and equivalents thereof known to those skilled in the art, and so forth. As well, the terms "a" (or "an"), "one or more" and "at least one" can be used interchangeably herein. It is also to be noted that the terms "comprising", "including", "composed of" and "having" can be used interchangeably.

Figure 1:
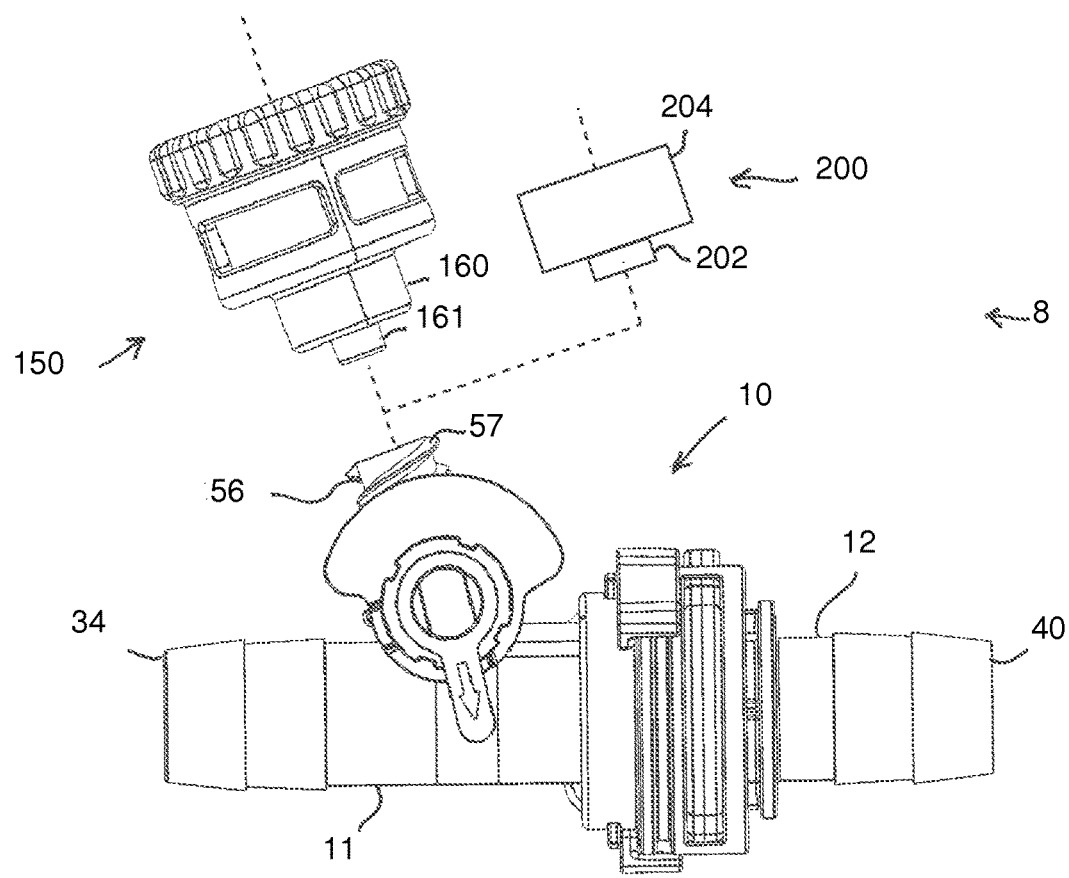
FIG. 1 is an exploded elevation view of a coupling assembly illustrating possible connections of a variety of fittings in accordance with an exemplary embodiment of the present invention.
Figure 2:
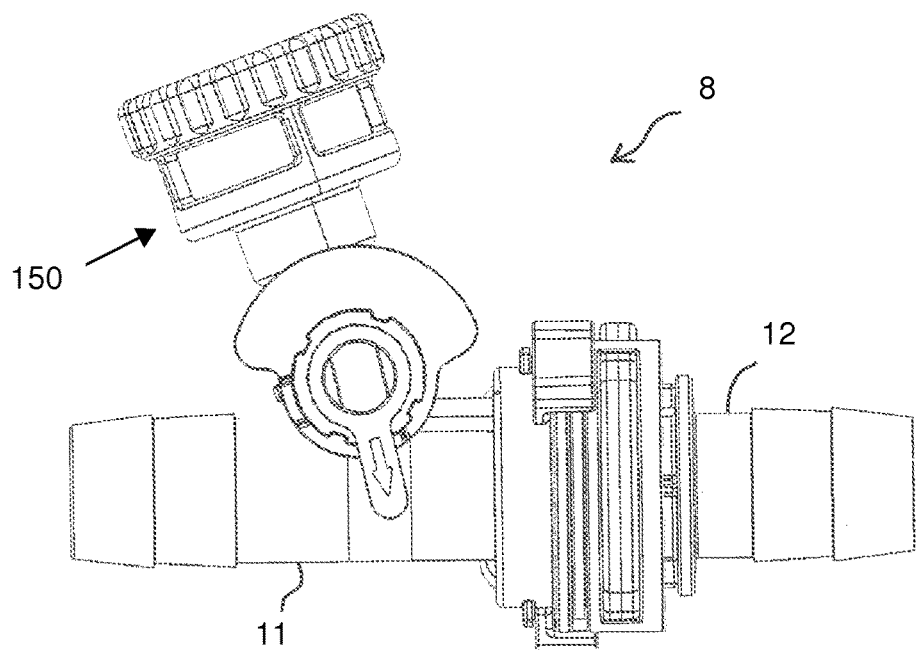
FIG. 2 is a side elevation view of the coupling assembly of FIG. 1, with an attached vent structure according to an exemplary embodiment of the present invention.
Figure 3:
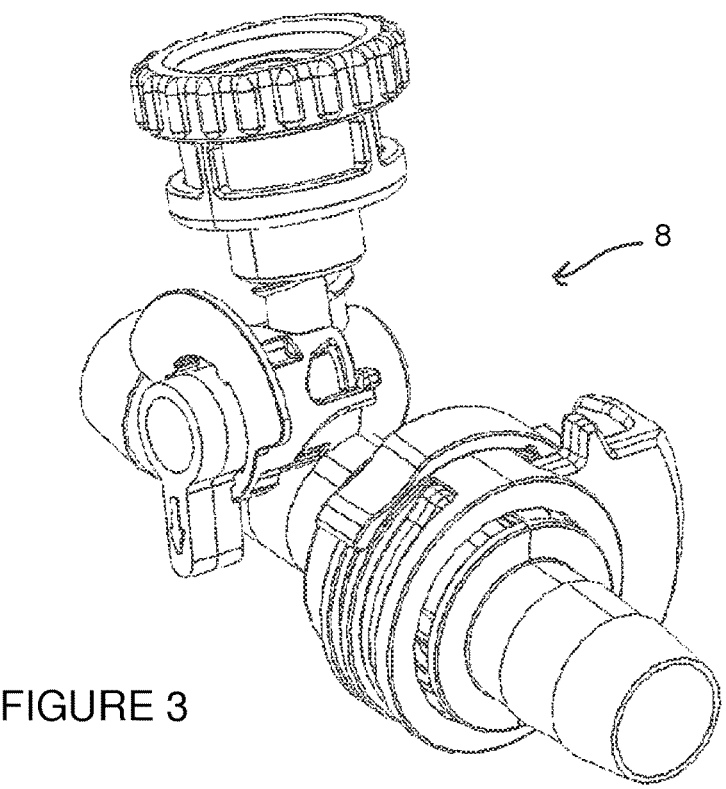
FIG. 3 is a perspective view of the embodiment of FIG. 2.
Figure 4B:
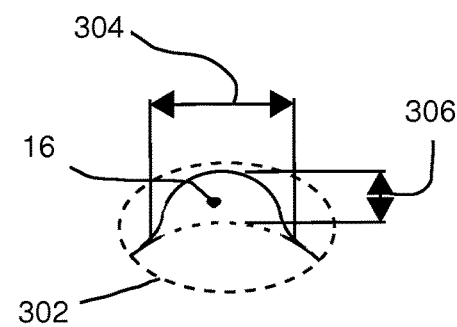
FIG. 4B is a partial view of the embodiment of FIG. 4A taken about border 302 and showing a width and height of the cavity, in accordance with an exemplary embodiment of the present invention.
Figure 4A:
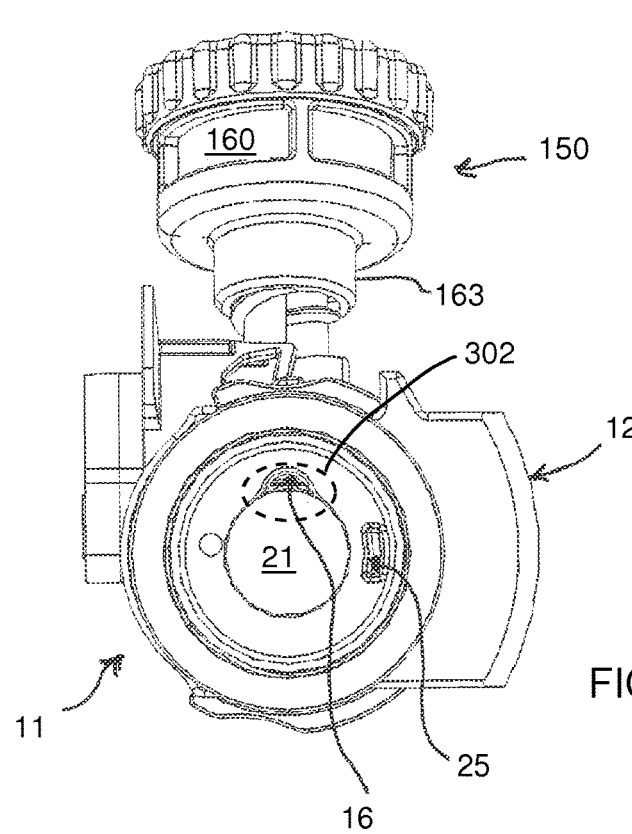
FIG. 4A is a side view of the embodiment of FIG. 2 with the male connector and corresponding seal element removed.

FIG. 1 illustrates a side elevation view of a fluid coupling assembly 8 useful for use in an extracorporeal blood circulation system (i.e. extracorporeal blood circuits, including those comprising for instance oxygenators, bubble sensors, cardiotomy reservoirs, and motorized pumps). The fluid coupling system may also be used for related medical applications involving the connection of two of more fluid conduits. More specifically, the fluid coupling assembly 8 comprises a coupling device 10 and an optional venting feature or vent assembly 150 for removing accumulated or captured air or bubbles within or near the inner portion of the coupling device 10 once assembled.

The coupling device 10 is preferably configured as a quick-release coupling device generally useful for connecting two or more conduits 32, such as tubing, pipes, catheters, cannula, hoses, etc. The optional venting assembly 150 may be configured as a de-aerator or vent mechanism connectable to the quick-release coupling 10 in either a fixedly attached manner, through for example integral fabrication, or a reversibly removable manner, through for example a male-luer to female-luer detachable connection as further shown in FIGS. 2-9.

The vent assembly 150 may self-seal upon contact with certain liquids. Alternatively, a plug or cap 200 as shown in FIG. 1 having a male luer 202 and a luer collar 204 may be employed instead of the vent assembly 150. The cap 200 can be used to seal the valve outlet lumen 56 extending from the coupling device 10 by threaded engagement with the external threads 57 of the valve outlet lumen 56. As shown in FIGS. 2-4A, when the vent assembly 150 is attached to the coupling device 10, the overall fluid coupling assembly 8 has a generally compact profile and an identifiable top vs. bottom orientation.

As shown best in FIGS. 5-9, the coupling device 10 comprises a female coupling member 11 and a male coupling member 12, each having a respective mating/connecting end 36, 38 and a free end 34, 40 (see FIG. 7). The free ends 34, 40 are preferably adapted for connecting to one or more conduits 32. These conduit attachment ends have a fastening mechanism 42, such as ridges and barbs, for establishing a friction-fit connection to separate conduits 32. Other types of connections are contemplated such as but not limited to solvent welding and/or adhesive bonding. The main body portions of the coupling device 10 are preferably made from a plastic such as polycarbonate, polystyrene, cyclic olefin copolymer (COC), or polyethylene terephthalate. In certain embodiments, the male coupling member 12 has at its connecting end 38 (also referred to as a first coupling end 38) a seal 13, preferably configured as an elastomeric seal member, which fits into a correspondingly shaped cavity 14 in the second coupling end 36 of female coupling member 11 when the male coupling member 12 is connected to the female coupling member 11.

When docked or connected, the two coupling members 11, 12 along with the seal 13 are preferably radially aligned and connected to each other so as to provide a transition between the surfaces of the male and female inner lumens 22, 23 that is free of gaps or spaces, or at most has negligible gaps or spaces. This resultant continuous and smooth transitional surface inhibits coagulation and turbulent blood flow at this transitional site. Additionally, the engagement between the two coupling members 11, 12 may provide for limited or restricted axial and radial "play" or movement, at least partially contributed by a partial compression of the seal 13 between the male and female coupling members 11, 12 when the coupling members 11, 12 are engaged in a locked position. This is most efficiently achieved when the seal 13 is formed from a material more compliant than the male and female coupling members 11, 12, and is connected to the male coupling member's 12 coupling end 38. Preferably the seal is formed out of a flexible, compliant and resilient material such as silicone rubber, natural rubber, nitrile butadiene rubber (NBR), carboxylated nitrile butadiene rubber (XNBR) or recognized equivalent elastomers and other elastomeric materials. In alternative embodiments, the seal member may instead be integrated into the female coupling member 11 so as to provide an inner surface for which the male coupling member 12 can engage in a sealing or gasket-like manner. In additional embodiments, an O-ring seal 19 may be employed to establish a secondary seal between an external surface of the male connector member 12 and an internal socket of the female connector member 11.

FIGS. 5, and 7-9 illustrate a projection or key 15 on the male coupling member 12 which extends lengthwise towards the female coupling member 11 from an edge forming the opening of mating end 38. The key 15 is configured to facilitate alignment between male coupling member 12 and the female coupling member 11. Preferably, the key 15 fits through an aperture or slot 7 in the seal 13 (best shown in FIG. 9) and extends through and beyond the seal 13 facilitating appropriate alignment with an internal pocket or key slot 25 of the female coupling member 11 (best shown in FIG. 7). An external back portion 25A of the pocket 25 may also be viewable in FIG. 9, providing internal spacing and room required to house the interior pocket 25. The combined use of the pocket 25 and key 15 helps establish and maintain alignment of each of the three components 11, 12, 13 with respect to each other, thereby restricting at least some, preferably all, rotational and longitudinal relative movement of the male coupling member 12 to the female coupling member 11 when the two are coupled.

Figure 13:
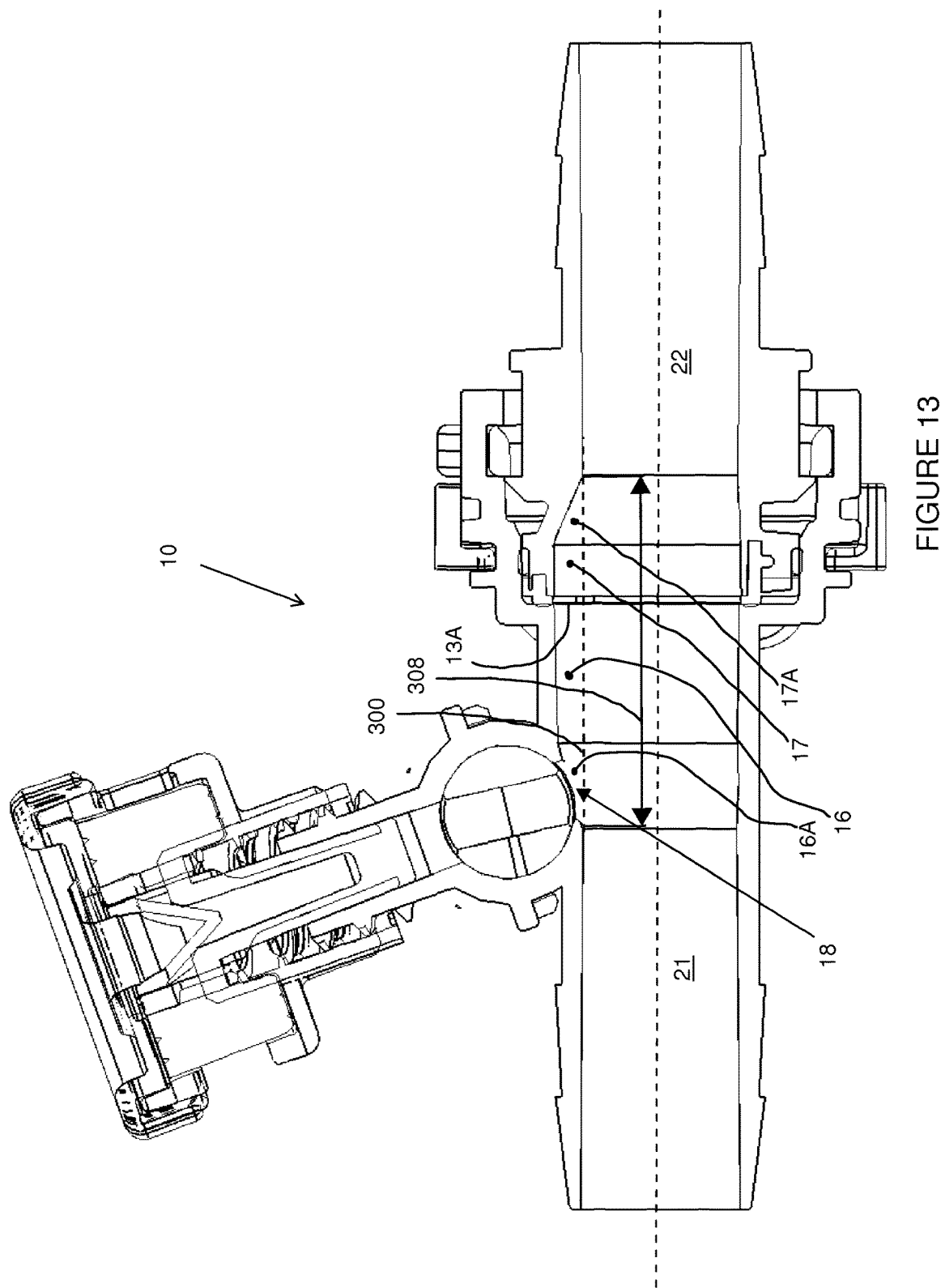
FIG. 13 is a cross-sectional view of the embodiments of FIGS. 3 and 4A, in accordance with an exemplary embodiment of the present invention.

As shown in FIG. 7, both male and female coupling members 11, 12 as well as seal 13 have mutually aligned internal portions producing a generally smooth luminal surface to transition between and flush with the luminal surfaces of each component, thus allowing for smooth conduction and transport of fluids therethrough when coupled together. As shown in FIGS. 7 and 13, the inner surface of annular seal 13 extends radially outward from a location flush with the adjoining inner surface of the male and female coupling member mating ends 36, 38 to an abutment surface of the coupling device, shown in this embodiment as a surface of female coupling member 11. In one embodiment, the transitional site defined by an inner surface of seal 13 and adjoining inner surface of male and female coupling members 11, 12 has a uniform cylindrical or spindle configuration. Such an arrangement minimizes or eliminates localized stagnation of blood as well as the possibility for turbulent flow to be induced. The lumen 21 of female connector member 11 preferably has an inner radius r1 and diameter dl similar in size to the lumen 22 of the male connector member 12.

One or more portions of the female coupling member, male coupling member or seal 13 may have an inner lumen cavity extension 16, 17 configured as a bulge, recess or outwardly extending protrusion region with respect to the adjoining luminal surface. This inner lumen cavity extension 16, 17 may be configured as a cavity defined by a portion of the inner surface of the coupling member extending from an axis of the male and female coupling members more radially outward than the adjoining luminal surfaces. In the embodiment shown in FIGS. 7 and 13, each of the male and female coupling members 11, 12 as well as the seal 13 has a lumen extension or expansion region (i.e., cavity or channel) formed by respective inner lumen cavity extensions 16, 17, and 13A. Each of the cavity extensions 16, 17, 13A are located towards the mating ends 36, 38 of the coupling members 11, 12 and exist along the thickness of the seal 13. When the male and female coupling members 11, 12 and the seal 13 are connected, the cavity extensions 16, 17 and 13A form a substantially continuous channel. Additionally as shown in FIGS. 7 and 13, transition regions 16A and 17A of respective cavities 16 and 17 are each tapered, slanted or contoured to merge gradually and form an overall smooth transition between lumens 21 and 22. As can be appreciated from FIGS. 5, 7, 9, 12 and 13, the male and female member lumens 21, 22 and the seal 13 may be configured to have a different cross-sectional profile taken through a plane normal to a luminal axis 49 along the length where the cavity extensions exist, as compared to other portions of the lumens 22,21. It should be noted that a functional space/region/cavity/channel may be formed from one or more of the cavities extensions 16, 17, 13A, with or without one or more of the cavity transition regions 16A, 17A.

Additionally as shown in FIGS. 7 and 13, the effective radius r2 of the cavity extensions 16,17,13A with respect the luminal axis 49 is larger than the radius r1 of the lumens 21,22, thereby providing a localized expanded effective inner diameter within these cavity regions 16, 17 or channel. This expanded effective inner diameter can additionally be appreciated as shown by the inclusion of segmented border line 300 of FIG. 13, which demarcates where the inner lumens formed by the coupling members 11,12 would exist in the absence of the cavity extensions 16, 17, 13A and their respective transition region(s). Additionally shown in FIG. 13 is a representation of the channel's length 308, which preferably is of a magnitude larger than the channel's width 304 and height 306 (see FIG. 4A).

Since the cavity regions 16, 17, 13A are located at the uppermost top superior portion of the coupling members 11, 12 and seal 13, and together may form a generally continuous channel between the coupling members 11,12, when oriented to be elevationally superior with respect to other portions of the lumens 21, 22, the channel formed by the cavity regions 16,17 can function to accumulate gas or gas bubbles. The bubbles are formed either incidentally through the process of connecting the coupling members, or by a natural accumulation of bubbles resulting from the flow of a bubble-carrying fluid through the couplings.

At the end of the transition region 16A and in proximity to the start of the cavity region 16 of the female connector member 11, a vent opening 18 is provided which is configured to allow for the aspiration of all the focused gases or bubbles accumulated within the channel formed by cavities 16, 17. This opening can be selectively occluded or allowed to function as a passage by the use of a valve such as a stopcock 64, or a removable cap 200. Additionally a vent device 150 configured to allow for selective fluids to pass through, can be employed to function as a self-sealing vent.

Figure 5:
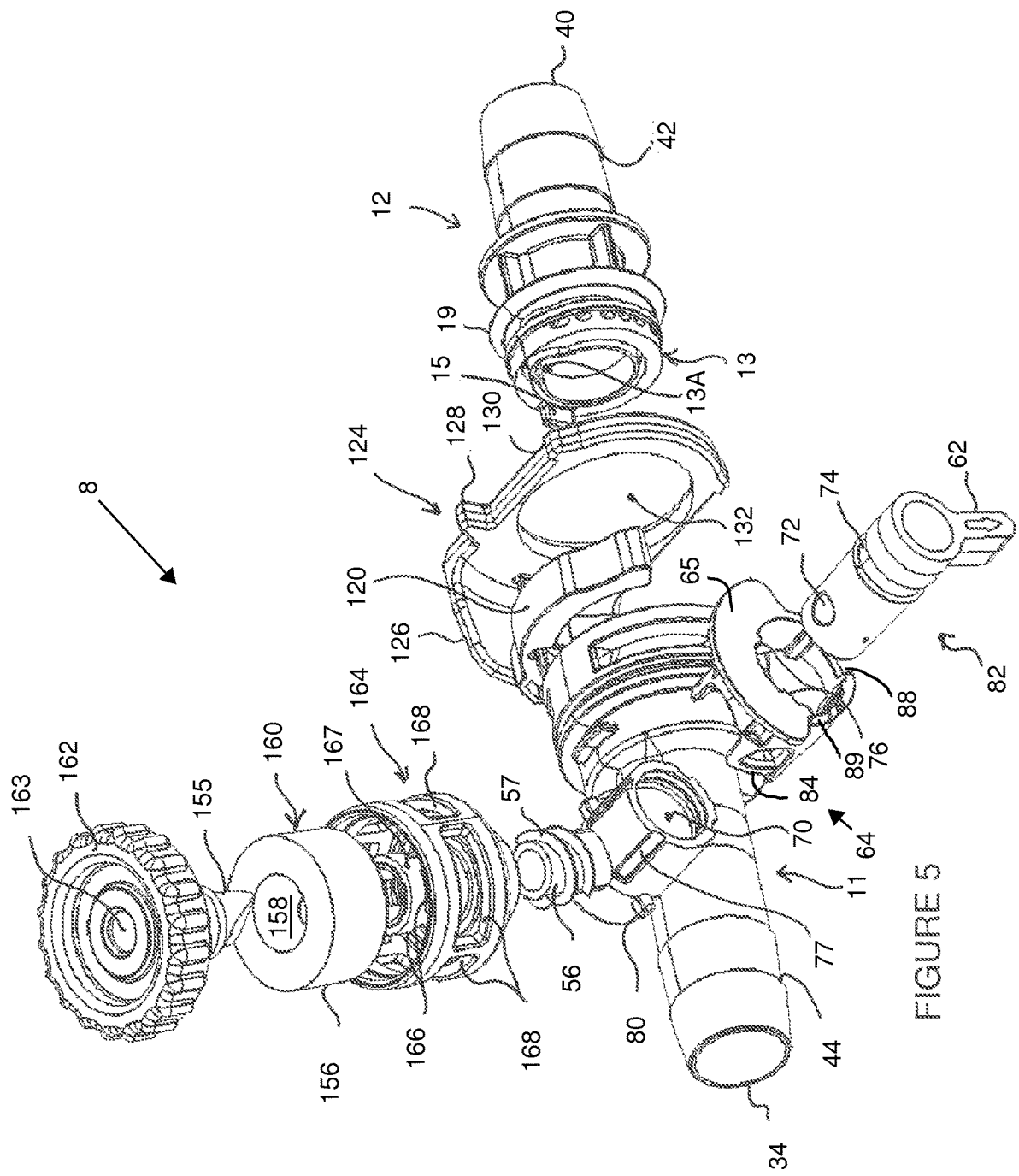
FIG. 5 is an exploded perspective view of the embodiment of FIG. 2.

Consistent with certain embodiments of the present disclosure, FIG. 5 illustrates in detail the components of the stopcock assembly 64, which primarily comprises a cylindrical plug-valve member 82 having a knob 62 on one end and a thru-hole bore 72 at the other end that operates with a receiving socket 70. A plastic socket adapter 65 snaps onto grooves 77 of an external surface of the socket 70 to facilitate the assembly of the stopcock 64 as well as provide for limited rotation of the plug-valve member 82 with respect to the socket 70 through recesses 88 and 89 which will be explained later in more detail. The socket adapter 65 is resiliently connected to the socket 70 through one or more cantilevered arms 84 (see FIGS. 11A-11C) which act as a as a cantilevered spring due to the arms shape and the existence of space 86 (see FIG. 9) which allows for deflection of the arms 84. The arms 84 are configured to align with and abut against the one or more contacting abutment(s) 80 that are integral to the socket's 70 external surface such that displacement of the socket adapter 65 towards the outlet lumen 56 causes the arms to bend and allow for the socket adapter to momentarily be displaced. Once released by the removal of force applied to the socket adapter, the arms release their stored energy and the socket adapter resumes its prior position.

As shown in FIG. 5, a plurality of protrusions or tabs 76 are located on the socket adapter 65 to align with a groove 74 on the plug-valve member 82. This arrangement allows for the rotation of the plug-valve member with respect to the socket 70 and socket adapter 65. As drawn in FIG. 7, the plug-valve member 82 has a bore 72 that may be aligned with the vent opening 18 and valve outlet lumen 56, allowing fluid communication therebetween.

Figure 11A:
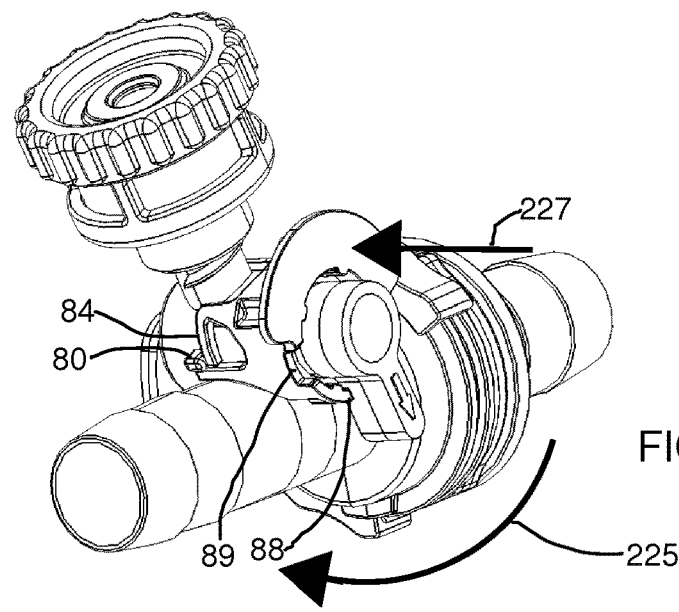
FIGS. 11A through 11C are isometric views of the embodiment of FIGS. 2 and 3, showing a valve knob at different orientations to control the opening and closing of a valve in accordance with exemplary embodiment of the present invention.
Figure 11B:
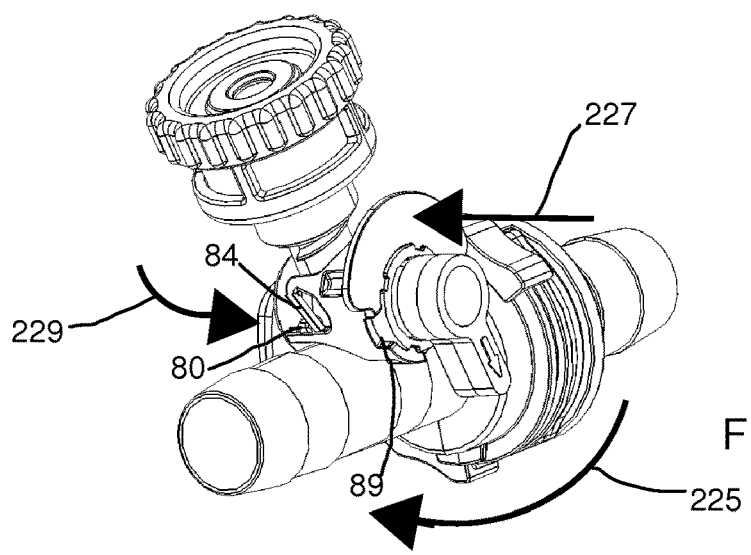
Figure 11C:
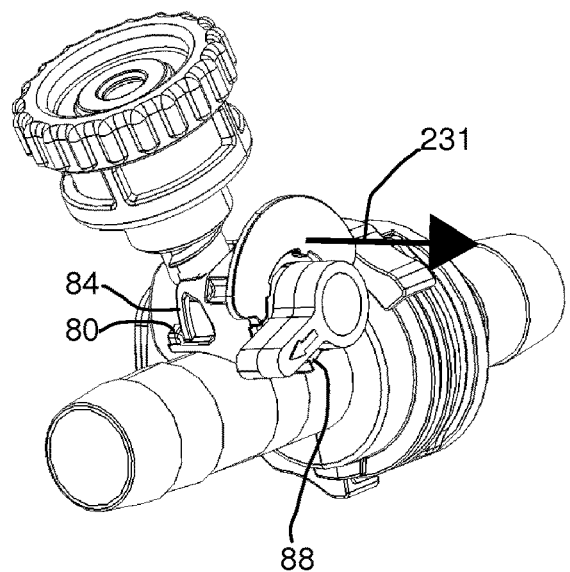
Figure 12:
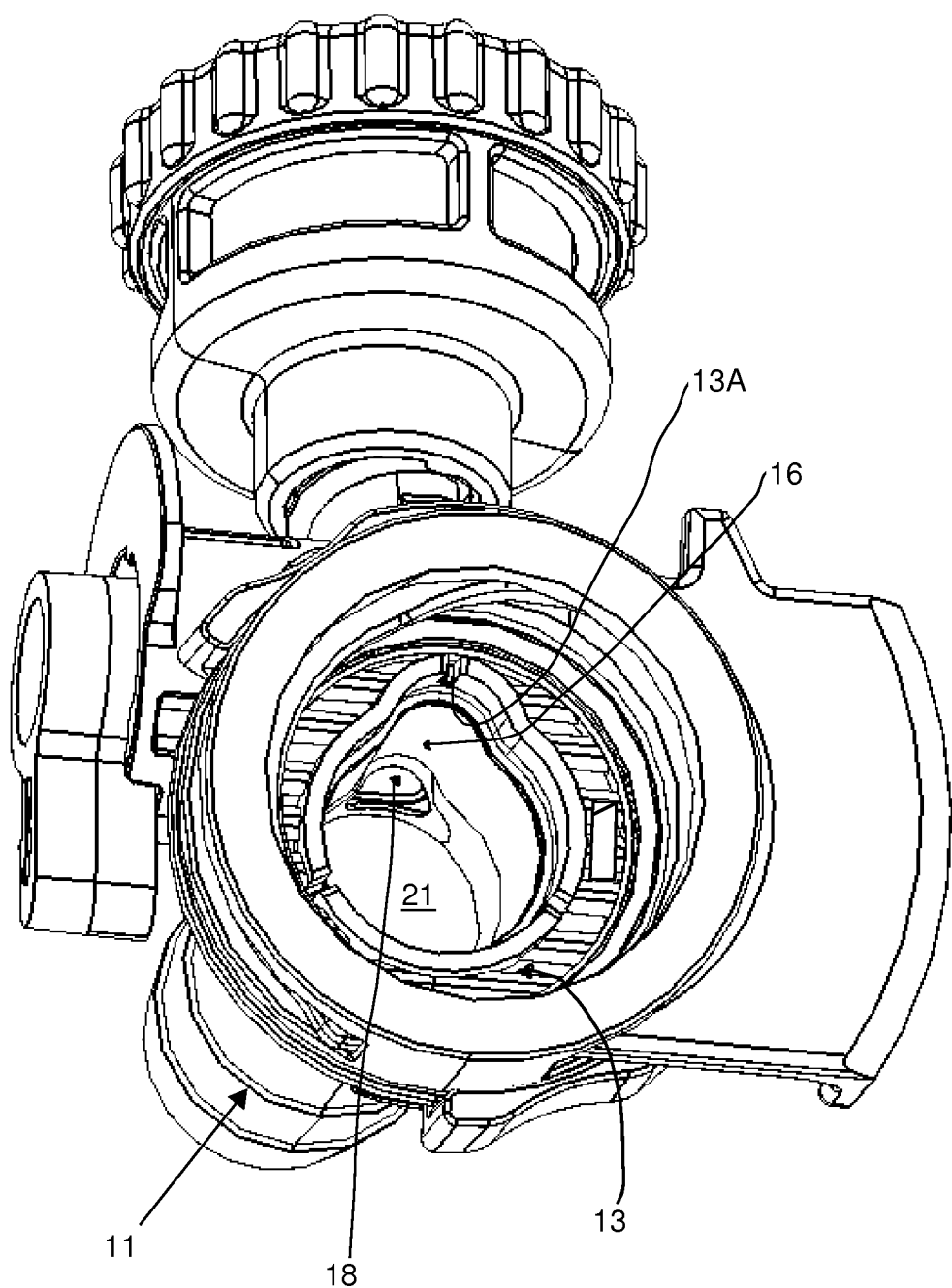
FIG. 12 is an isometric view similar to the embodiment of FIG. 4A but with only the male coupling member removed, thereby showing a channel formed by the female coupling member and the seal, the channel leading towards a vent opening in accordance with an exemplary embodiment of the present invention.

FIGS. 11A through 11C depict the closing of the stopcock valve from its open position of FIG. 11A to its closed position of FIG. 11C. When the knob 62 is moved from a first position along a first path (see arrow 225 of FIGS. 11A and 11B) to a second position (see FIG. 11C), the stopcock adjusts from a first state wherein vent opening and valve outlet lumen 56 are in fluid communication via the bore 72 (see FIG. 7), to a second state wherein a portion of the plug valve member misaligns the bore 72 with respect to the vent opening 18 and valve outlet lumen 56, thereby closing the valve (see FIG. 10).

In additional embodiments, the stopcock portion of the connector assembly 10 may employ a lock feature to ensure that the plug valve member 82 is in only one of the aforementioned first or second states. The recesses 88 and 89 on the socket adapter 65 are sized to accommodate the width of knob 62. FIGS. 11A and 11B depict the first state wherein the valve is opened and the knob 62 is partially seated within recess 88 and therefore restricted to rotate. When a lateral force is applied against the socket adapter 65 (see arrow 227), the socket adapter is displaced due to the compression and flexing of arms 84 (see FIG. 11B), thereby eliminating the interference previously existing between the recess 88 and the knob 62 and allowing rotation of the knob to be moved along arc 225 towards a second position (see FIG. 11C) consistent with the second state of the valve. When the knob 62 reaches its second position, the arms 84 release of the socket adapter push the socket adapter 65 back to its original position whereby the knob 62 is now confined within recess 89 instead of recess 88. The above steps can be reversed to move the knob 62 back to the first position consistent with FIGS. 11A and 11B in the event it is desired to re-open the stopcock valve.

The coupling device 10 may also benefit from the use of a locking mechanism as described herein. The locking mechanism 120 facilitates the coupling of the male and female coupling members such that the coupling members 11, 12 are secured against unintentional loosening or separation, and preferably maintains some degree of axial compression of the seal 13. By displacing a release element 124 in the direction of the arrows shown in FIG. 9 through application of a force on the tab 126, the male and female coupling members 11, 12 are selectively allowed to reversibly engage and disengage each other. As shown in FIGS. 5 and 9, stop members 130 and 128 of release element 124 limit travel of the release element with respect to the female coupling member 11 while a clip 20 helps confine and guide the release element 124 to only travel towards and away from the female coupling member 11. Thereafter, the fluid passage can be selectively released or decoupled as desired by the user through activation of tab 126 of the quick coupling device 10.

Once the male and female coupling members 11, 12 are connected and establish a fluidic connection between two fluid conduits, and provided that fluid communication is established between the vent opening 18 and the vent lumen outlet 56, the aspiration of bubbles or gasses collected in cavity regions 16, 17 can be realized. The user will handle and orient the quick-release coupling device 10 such that the cavity regions 16, 17 are at their highest elevation, superior with respect to other parts of the lumens 21, 22 such that any gases located within the region or interface of the coupling will rise and concentrate towards the cavity regions 16, 17. This can be readily appreciated as shown for example in FIG. 7, wherein bubbles or gases will be allowed to follow the path 192 towards the vent lumen outlet 56 and eventually to atmosphere depending on whether or not a venting device or de-aerator apparatus 150 is attached to the coupling assembly 10. In certain embodiments of the present disclosure, aspiration involves a self-sealing venting technology within the venting device.

FIGS. 5-7 depict components and details of the vent assembly/device 150, and show a housing assembly comprising an upper housing or cap 162 and a lower housing 164. The lower housing 164 has a lumen that can establish fluid communication with the valve outlet lumen 56 of the connector assembly 10. In accordance with this disclosure, the valve outlet lumen 56 may be construed as defined by a third end of the female coupling member 11 as shown in FIG. 5. Preferably, the lower housing 164 has a male luer 161 construction to connect to the female luer of the valve outlet lumen 56. Additionally a luer-lock collar 163 is preferably utilized to allow for a secured reversible connection to be made between the male luer 161 of the vent assembly 150 and the female luer of valve outlet lumen 56. Spaced between the upper and lower housing is a porous plug or vent structure 160 shaped as a thick washer or doughnut, having a central bore 158. The vent structure 160 is comprised of a porous material or a porous membrane and is preferably made from a hydrophobic material. Examples of such materials include polyethylene, polypropylene or Teflon. Such a material or membrane can allow for gases to pass through, however may selectively block certain liquids such as hydrophilic blood due to the related surface tensions of the blood. The compact porous materials can be produced for example through a powder sintering process of the above-described substances and are available for example from Porex Corporation of Fairburn, Ga. When using membranes instead of or in conjunction with a porous plug, the membrane can be reinforced as necessary by a supporting body or frame structure. In use, when a mixture of a hydrophilic liquid and gas make contact with such a porous surface of the venting device 150, the gas can escape through the plug while the liquid instead will wet the pores and therefore block penetration and transport through the porous structure 160, preventing the liquid from reach an external surface.

FIG. 7 illustrates a central cavity 51 located between the upper 162 and lower housing 164 of the venting device 150. In various embodiments of the present disclosure, a slit valve 55 encloses the central cavity's 51 upper end while the lower end is in fluid communication between an internal lumen of the male luer 161, the lower end of the cavity 51, and the vent material 160. Gas or bubbles accumulating in the cavity extensions of the lumens of the coupling device 10 can pass from the valve outlet lumen 56 into the venting device 150 and then escape laterally through the vent material 160 in the direction of the arrows 53 and 54, while hydrophilic liquids are prevented from exiting through the vent material 160 and remain contained within the venting device and coupling device. As mentioned previously, this type of arrangement reduces the probability of exposure of the blood internal to the coupling device to be exposed to pathogens which could lead to infection of the blood and patient.

In a certain embodiments of the present disclosure, the aforementioned slit valve 55 can be utilized to provide additional access to the internal lumens 21, 22 of the fluid path formed by the coupling assembly 10. This can be useful to a medical practitioner in the event he or she wishes to (i) add a liquid from the outside of the blood circuit into the tubes, pipes or catheters connected to the coupling device 10 and/or (ii) remove liquid from the circuit such as during a process of sampling blood from the inside of the blood circuit for diagnostic analysis and monitoring. Therefore, it is possible to either provide liquid drugs and medications to the bloodstream when syringe access is desired without the need to further cannulate the patient.

The slit valve (or duckbill valve) preferably has two internal walls are moved apart from each other when a device comprising a male luer taper such as a syringe is inserted into a cavity 163 of the top housing 162, thereby opening the valve. The walls of the slit valve are resiliently biased to provide for self-sealing performance when the male luer taper of a syringe is removed from the valve. The slit valve as well as other self-closing valves such as dome valves may be employed to accomplish a similar effect of achieving a resealable access point.

Method of Use

The previously described coupling device may be provided pre-connected to fluid conduits or alternatively may be a stand-alone configuration. Preferably the coupling device is received by the user sterilized (e.g., $10^{-3}$ sterility assurance level or better). If a stand-alone configuration is needed to couple two fluidic conduits, the user will connect the free ends 34, 40 of the female and male connector members to the appropriate conduit, tubing or device. The male and female connector members 11, 12 may be provided already connected, or alternately arrive separate. If separate, the user will align the connector members together so that the extension cavities 16, 17, 13A are in alignment with each other. Alignment indicia such as external markings, notches, protrusions, etc., may be employed on one or both of the connector members 11, 12 to facilitate alignment.

In embodiments where the vent device 150 is not utilized, the stopcock valve is moved to the closed position (see FIGS. 11C and 10) prior to the filling of the circuit or conduits connected to the connector device 12 with blood. When the venting device 150 is employed, the stopcock valve may be moved to either the open or closed positions.

Blood is allowed to fill the circuit and the connector device is maintained in an upright orientation (see either FIG. 1 or 2) with the valve outlet lumen 56 facing upwards at an angle with respect to the horizon such that the cavity extensions 16,17 are at the highest elevation as compared to any other portion of the lumens 21,22. The stopcock valve is moved to the open position allowing trapped gas or air bubbles collected at cavity extension regions 16,17 to exit the lumens 21,22 via the vent 18 and pass towards the vent device 150 or optionally just vent to atmosphere. When the vent device is employed, the gas or air bubbles exit the vent device 150 by passing through the porous structure 160 while blood remains enclosed within the vent device 150.

If delivery of medicaments to the connector device 10 is needed, the luer tip of a syringe may be inserted into the valve 55 to cause it to open, and when the stopcock valve is in the open position, distal displacement of the syringe plunger will cause delivery of the medicaments to the lumens 21,22 and the fluid paths or circuits connected to the lumens. If instead blood sampling is desired, the syringe plunger can be displaced proximally such that fluid from the lumens 21,22 will be drawn into the syringe barrel or chamber and typically sent for diagnostic testing purposes.

Those skilled in the art can appreciate from the foregoing description that the present invention can be implemented in a variety of forms and is not limited to quick connect couplings or venting members for blood circulation or extracorporeal blood circuits. The coupling of the present invention can be used and/or connected to other devices requiring venting of air, gasses or bubbles from liquid fluids. Further, the inventive modularity aspects of the present invention can be applied to other devices, e.g., medical devices, that would benefit from multiple configurations suited for different operating conditions and environments. Therefore, while the embodiments of this invention have been described in connection with particular examples thereof, the true scope of the embodiments of the invention should not be so limited since other modifications and variations will become apparent to the skilled practitioner upon a study of the drawings and specification. Such modifications and variations are considered to be within the purview and scope of the appended claims and their equivalents.

What is claimed is:

1. A connector system for use in connecting fluidic conduits, wherein the system comprises:
   a male connector comprising
      a first coupling end comprising a first inner surface defining a first opening in communication with a lumen of the male connector; and
      a second end for establishing fluid communication with a first conduit securable with respect to the male connector;
   a female connector comprising
      a second coupling end comprising a second inner surface defining a second opening in communication with a lumen of the female connector and detachably connectable to the first coupling end; and
      a third end for establishing fluid communication with a second conduit;
   a seal operatively associated with the male connector and the female connector, wherein the seal is connected to at least one of the male connector and the female connector such that when the male connector and the female connector are coupled with respect to each other, the seal is disposed between a portion of the first coupling end and the second coupling end, forming a fluid tight connection between the male connector and the female connector, wherein an inner surface of the seal, the first inner surface and the second inner surface form a continuous and smooth transitional surface, wherein the inner surface of the seal, the first inner surface and the second inner surface comprise a lumen cavity extension configured as a bulge, recess or outwardly extending protrusion region, wherein the lumen cavity extension has a smooth continuous surface that stretches across the male coupling member, the female coupling member, and the seal; and
   a vent assembly comprising a vent aperture disposed to permit venting of fluid from the lumen of the male connector and the lumen of the female connector when the male connector and the female connector are coupled together; and a valve disposed to open and close access to the lumen of the male connector and the lumen of the female connector when the male connector and the female connector are coupled together, and wherein the male connector and the female connector when assembled have an upright orientation, and the lumen cavity extension is at an elevation superior to the lumen of the male connector and the lumen of the female connector when the connector system is in the upright orientation so that the lumen cavity extension is disposed to accumulate gas or gas bubbles from the lumen of the male connector and the lumen of the female connector, wherein the vent assembly vents the accumulated gas or gas bubbles from the lumen cavity extension.

2. The connector system of claim 1, wherein the seal is fixedly positioned with respect to a portion of the first coupling end and the second coupling end so as to inhibit or prevent movement in a radial and axial direction when the seal is secured between the male coupling end and the female coupling end.

3. The connector system of claim 1, wherein one of the male connector and the female connector has a key and the other of the male connector and the female connector has a key slot for receiving the key such that the key is engaged with the key slot when the male connector and the female connector are coupled.

4. The connector system of claim 3, wherein the seal is adapted to not block the key from engaging the key slot.

5. The connector system of claim 3, wherein the engagement between the key and the key slot when the male connector and the female connector are coupled restricts radial movement of the male connector and the female connector with respect to each other.

6. The connector system of claim 1, wherein the lumen cavity extension is configured as a channel having a length longer than its width.

7. The connector system of claim 1, wherein the male connector and the female connector are sterilized to a sterility assurance level equal to or greater than 10-3 SAL, and wherein the fluidic conduits are part of an extracorporeal blood circulation system.

8. The connector system of claim 7, wherein the extracorporeal blood circulation system comprises a motorized pump and at least one of an oxygenator, a heat exchanger for controlling the temperature of blood passing through the extracorporeal blood circulation system, a cardiotomy reservoir, and a bubble sensor.

9. A connector system for use in connecting conduits of an extracorporeal blood circulation system, wherein the system comprises:
a male connector comprising:
a first coupling end comprising a first inner surface defining a first opening in communication with a lumen of the male connector; and
a second end for establishing fluid communication with a first conduit securable with respect to the male connector;
a female connector comprising:
a second coupling end comprising a second inner surface defining a second opening in communication with a lumen of the female connector and detachably connectable to the first coupling end; and
a third end for establishing fluid communication with a second conduit;
a seal operatively associated with the male connector and the female connector, wherein the seal is positionable between the male connector and the female connector such that when the male connector and the female connector are coupled with respect to each other, the seal is disposed between a portion of the first coupling end and the second coupling end, forming a fluid tight connection between the male connector and the female connector so that an inner surface of the seal, the first inner surface and the second inner surface form a continuous and smooth transitional surface, wherein when the connector system is oriented in an upright orientation, a cavity extending from the male connector to the female connector and in fluid communication with the lumen of the male connector and the lumen of the female connector, wherein the cavity is at an elevation superior to the lumen of the male connector and the lumen of the female connector, wherein the cavity is configured from cavity extensions of the male connector, the female connector and the seal so as to form a channel providing a smooth continuous surface that tapers at one or both ends towards, and is continuous with, the lumen of the male connector and the lumen of the female connector while the male connector and the female connector are coupled to each other, and wherein the cavity is disposed to accumulate gas or gas bubbles from the lumen of the male connector and the lumen of the female connector; and
a vent device comprising a vent aperture and vent structure, wherein the vent structure is porous and is disposed to allow gas to pass through the cavity so as to exit through the vent aperture while the vent structure prevents liquid from exiting through the vent aperture.

10. A quick-coupling connector system operable to connect fluid conduits, wherein the connector system is associated with a venting device that is detachably connected to a sealable gas vent of the connector system, and the venting device comprises:
a cavity containing porous material or a semi-permeable membrane, wherein the connector system is configured to connect to fluid carrying tubes or pipe lines at tube connection areas of an extracorporeal blood circuit, and the connector system comprises a male coupling member and a female coupling member that are detachably connectable to each other in a fluid-tight manner, wherein a seal is arranged at a mating end of the male coupling member that permits insertion without play in radial and axial directions into a corresponding recess of the female coupling member, and upon connection of the male coupling member to the female coupling member a gap-free and step-free transition is formed between a lumen of the male coupling member and a lumen of the female coupling member, wherein the male coupling member and the female coupling member and the seal each possess a cavity extension that together form a channel disposed to accumulate gas or gas bubbles from the lumen of the male coupling member and the lumen of the female coupling member, wherein the channel has a smooth continuous surface that stretches across the male coupling member, the female coupling member and the seal, wherein the venting device vents the accumulated gas or gas bubbles from the channel.

11. A quick-coupling connector system operable to connect fluid conduits, wherein the connector system is associated with a venting device that is detachably connected to a sealable gas vent of the connector system, wherein the connector system is configured to connect to fluid carrying tubes or pipe lines at tube connection areas of a fluid circuit, and the connector system comprises a male coupling member and a female coupling member that are detachably connectable to each other in a fluid-tight manner, wherein a seal is arranged at a mating end of the male coupling member that permits insertion into a corresponding recess of the female coupling member, and upon connection of the male coupling member to the female coupling member a gap-free and step-free transition is formed between fluid-carrying lumens of the male coupling member and the female coupling member, wherein the male coupling member and the female coupling member and the seal each possess a cavity extension that together form a channel disposed to accumulate gas or gas bubbles from lumens of the male coupling member and the female coupling member, wherein the channel has a smooth continuous surface that stretches across the male coupling member, the female coupling member and the seal, wherein the sealable gas vent vents the accumulated gas or gas bubbles from the channel.

12. The connector system of claim 11, wherein the fluid circuit is an extracorporeal blood circuit.

* * * * *